US009585997B2

(12) United States Patent
Suzuki et al.

(10) Patent No.: US 9,585,997 B2
(45) Date of Patent: Mar. 7, 2017

(54) LEUCOCYTE REMOVAL FILTER

(75) Inventors: Ikuhiro Suzuki, Takasago (JP); Hiroshi Tone, Takasago (JP); Masaru Nakatani, Takasago (JP)

(73) Assignee: KANEKA CORPORATION, Osaka (JP)

( * ) Notice: Subject to any disclaimer, the term of this patent is extended or adjusted under 35 U.S.C. 154(b) by 91 days.

(21) Appl. No.: 13/881,289

(22) PCT Filed: Oct. 21, 2011

(86) PCT No.: PCT/JP2011/074308
§ 371 (c)(1),
(2), (4) Date: Jul. 11, 2013

(87) PCT Pub. No.: WO2012/057029
PCT Pub. Date: May 3, 2012

(65) Prior Publication Data
US 2013/0277297 A1 Oct. 24, 2013

(30) Foreign Application Priority Data
Oct. 25, 2010 (JP) ................................ 2010-238839

(51) Int. Cl.
*B01D 39/00* (2006.01)
*A61M 1/36* (2006.01)

(52) U.S. Cl.
CPC ............ *A61M 1/36* (2013.01); *A61M 1/3633* (2013.01); *B01D 2239/125* (2013.01); *B01D 2239/1233* (2013.01)

(58) Field of Classification Search
USPC ....... 210/503, 767, 800, 806, 483, 473, 504, 210/505
See application file for complete search history.

(56) References Cited

U.S. PATENT DOCUMENTS

| | | | | |
|---|---|---|---|---|
| 5,407,581 | A | 4/1995 | Onodera et al. | |
| 6,267,898 | B1 * | 7/2001 | Fukuda et al. | 210/767 |

FOREIGN PATENT DOCUMENTS

| | | | |
|---|---|---|---|
| JP | 2-203909 | A | 8/1990 |
| JP | 6-7429 | A | 1/1994 |
| JP | 8-201384 | A | 8/1996 |
| JP | 2003-180822 | A | 7/2003 |
| JP | 2005-336080 | A | 12/2005 |
| JP | 2009-167128 | A | 7/2009 |

OTHER PUBLICATIONS

Yun et al., Chemical Engineering Science 62 (2007) 4751-4759.*
Singha et al., 2012, International Journal of Textile Science, 1(1): 7-14.*
Spurny, Advances in Aerosol Filtration, 1998, p. 165.*
Sommerville et al., 2004, pp. 1-6, Fundamental principles of fibre fineness measurement.*
International Preliminary Report on Patentability, and Translation of Written Opinion of the International Searching Authority, dated May 14, 2013, for International Application No. PCT/JP2011/074308 (Forms PCT/IB/373 and PCT/ISA/237).
International Search Report for PCT/JP2011/074308 mailed on Jan. 31, 2012.

* cited by examiner

*Primary Examiner* — Allison Fitzsimmons
(74) *Attorney, Agent, or Firm* — Birch, Stewart, Kolasch & Birch, LLP

(57) ABSTRACT

The present invention aims to provide a leukocyte depletion filter that has both higher leukocyte removal performance and higher blood permeability than conventional filters. The leukocyte depletion filter according to the present invention includes a filter material having an average fiber diameter of 0.30 to 1.60 μm and a coefficient of variation of fiber diameter of at least 0.40 but not more than 1.20.

5 Claims, No Drawings

LEUCOCYTE REMOVAL FILTER

TECHNICAL FIELD

The present invention relates to a leukocyte depletion filter material and a leukocyte depletion filter for the removal of leukocytes from leukocyte-containing fluid such as blood.

BACKGROUND ART

Blood products for use in blood transfusions include, for example, whole blood products prepared by adding an anticoagulant to blood collected from donors, as well as red blood cell products, platelet products and plasma derivatives which are prepared by separating blood components required by a particular recipient from the whole blood products. The leukocytes contained in these blood products, however, are known to cause side effects (e.g. fever response, transfusion-related acute lung injury) and cytomegalovirus infections, and also act as an alloantigen to induce a recipient to produce antileukocyte antibodies, leading to platelet refractoriness.

In order to prevent these incidents, the so-called leukocyte-depleted blood transfusion, in which a blood product is transfused after the removal of the leukocytes contained in the blood product, has become common. The methods for removing leukocytes from a blood product includes two methods, namely a centrifugation method that utilizes the specific gravity difference between the blood components, and a filtration method that utilizes a porous material as a filtering medium. The filtration method has been widely used because it has high leukocyte removal performance, allows easy operation, and costs low.

Meanwhile, long storage of blood products can cause the leukocytes to produce pyrogenic cytokines during the storage, and can lead to death and breakage of the leukocytes that have engulfed viruses or bacteria, allowing pathogens to be spread in the blood for transfusion. Transfusion of such blood containing viruses or bacteria may cause infection in the recipient. Hence, leukocytes need to be removed before storage of blood products.

For prevention of such side effects related to blood transfusion, the Ministry of Health, Labour and Welfare notified the Japanese Red Cross Society of the draft guidance on prestorage leukocyte reduction (to a number of residual leukocytes of not more than $1\times10^6$/product) for all products for transfusion in 2003. Then leukocyte depletion filters started to be used for platelet products from donated platelets in 2004, for plasma derivatives from donated plasma in 2005, and for red blood cell products from whole blood in 2006.

Currently used leukocyte depletion filters have leukocyte removal performance (−Log 4) enough to give a number of residual leukocytes of not more than $1\times10^5$/product (Non-Patent Literature 1). Still, there is a market demand for filters having higher leukocyte removal performance than the currently used filters so that critical side effects that can be caused by leukocytes transfused into a patient can be completely prevented.

To prevent such side effects, the amount of a filter material to be used has been increased. With the conventional leukocyte depletion filters, however, it is difficult to achieve high leukocyte removal performance enough to completely prevent side effects when the amount of a filter material to be used is just increased.

The following methods for solving such a problem by using a nonwoven fabric as the filter material are known in the art: a method of reducing the average fiber diameter, a method of increasing the pack density, and a method of employing a nonwoven fabric with a more uniform fiber diameter distribution (Patent Literature 1). If these methods are actually employed to enhance the performance so as to give a number of residual leukocytes of not more than $1\times10^4$/product, the pressure loss in the filter part when a blood product passes through the filter is increased as the leukocyte removal performance is enhanced. As a result, unfortunately, the blood processing speed extremely decreases before completion of processing for the expected amount of blood.

Moreover, in many cases, the following approaches for blood filtration for prestorage leukocyte reduction are employed in parallel: room-temperature filtration which involves filtering at room temperature within one day after blood collection, and cold-storage filtration which involves filtering after storage for about one to three days in a refrigerator. The cold-storage filtration tends to take more time for filtration. Therefore, leukocyte depletion filters are required to have shorter time for filtration in cold-storage filtration.

CITATION LIST

Patent Literature

Patent Literature 1: JP H02-203909 A

Non Patent Literature

Non Patent literature 1: "Japanese Journal of Transfusion Medicine", Vol. 46, No. 6: 521-531, 2000

SUMMARY OF INVENTION

Technical Problem

The present invention aims to provide a leukocyte depletion filter that has both higher leukocyte removal performance and higher blood permeability than conventional filters. The invention also provides a leukocyte depletion filter that achieves high leukocyte removal performance and high blood permeability for refrigerated blood.

Solution to Problem

The present inventors have made intensive studies on leukocyte depletion filters having both high leukocyte removal performance and high blood permeability to solve the problem. As a result, they have found that both very high leukocyte removal performance and high blood permeability can be achieved using a filter having a reduced average fiber diameter when the fiber diameter distribution is controlled to be in a predetermined range, thereby having completed the present invention.

That is, the present invention relates to a leukocyte depletion filter material, including fibers that have an average fiber diameter of 0.30 to 1.60 μm and a coefficient of variation of fiber diameter of at least 0.40 but not more than 1.20.

The filter material preferably has an average pore size of 4.0 to 20.0 μm.

The filter material preferably has a bulk density of 0.05 to 0.40 $g/cm^3$.

The filter material preferably contains a hydrophilic polymer at least on a surface of the fibers.

The present invention also relates to a leukocyte depletion filter, including a receptacle having fluid inlet and outlet, and the first leukocyte depletion filter material packed in the receptacle.

In the leukocyte depletion filter, the first leukocyte depletion filter material is preferably packed in the form of a single layer or a laminate of layers oriented in a fluid flow direction.

The leukocyte depletion filter preferably further includes a different second leukocyte depletion filter material located upstream and/or downstream of the first leukocyte depletion filter material.

Preferably, the leukocyte depletion filter includes the second leukocyte depletion filter material located upstream of the first filter material, and the second leukocyte depletion filter material includes fibers that have an average fiber diameter of 1.00 to 4.00 μm, wherein the average fiber diameter is greater than the average fiber diameter of the fibers included in the first leukocyte depletion filter material.

The leukocyte depletion filter preferably satisfies the following formulas (a) and/or (b):

$$|A-B|<0.30 \quad (a)$$

$$0.10 \leq A \times B \leq 1.00 \quad (b)$$

wherein A represents the coefficient of variation of fiber diameter of the first leukocyte depletion filter material, and B represents a coefficient of variation of fiber diameter of the second leukocyte depletion filter material.

The leukocyte depletion filter preferably includes a pre-filter material for removal of fine aggregates, located upstream of the leukocyte depletion filter material.

The present invention also relates to a leukocyte depletion system, including: the leukocyte depletion filter, a blood collection bag connected upstream of the leukocyte depletion filter, and at least one blood bag connected downstream of the leukocyte depletion filter.

Advantageous Effects of Invention

Use of a leukocyte depletion filter including a filter material having an average fiber diameter of 0.30 to 1.60 μm and a coefficient of variation of fiber diameter of at least 0.40 but not more than 1.20 enables to achieve both higher leukocyte removal performance and higher blood permeability than conventional filters.

Moreover, a leukocyte depletion filter has still higher blood permeability and thus achieves high leukocyte removal performance and high blood permeability even when refrigerated blood is applied, if the filter includes a first filter material having an average fiber diameter of 0.30 to 1.60 μm and a coefficient of variation of fiber diameter of at least 0.40 but not more than 1.20, and a second filter material having a greater average fiber diameter than the first filter material, located upstream of the first filter material.

DESCRIPTION OF EMBODIMENTS

The leukocyte depletion filter material of the present invention features an average fiber diameter of 0.30 to 1.60 μm and a coefficient of variation of fiber diameter of at least 0.40 but not more than 1.20. The leukocyte depletion filter material refers to a filter material for selectively removing leukocytes from a leukocyte-containing fluid such as blood.

The form of the leukocyte depletion filter material preferably offers a large surface area in terms of frequency of contact with blood. Specific examples of the form include fabrics, nonwoven fabrics, and fibrous structures such as fibrous and filamentous forms. Particularly, fabrics and nonwoven fabrics are preferred in terms of the leukocyte adsorption capacity and the handleability as a separator, and nonwoven fabrics are most preferred because they can come into contact with leukocytes at multiple points. Here, a nonwoven fabric refers to a fabric-like material in which fibers or fiber assemblies are chemically, thermally, or mechanically bonded without being knitted or woven. Those mechanically bonded include fibers that retain a certain form due to, for example, friction between the fibers in contact with each other or tangles of the fibers.

The filter supporting substrate included in the leukocyte depletion filter material may be any substrate that does not easily damage blood cells. Examples of the supporting substrate include polyester, polyolefine, polyacrylonitrile, polyamide, polystyrene, polyalkyl(meth)acrylate, polyvinyl chloride, polychloroprene, polyurethane, polyvinyl alcohol, polyvinyl acetate, polysulfone, polyether sulfone, polybutadiene, butadiene-acrylonitrile copolymers, styrene-butadiene copolymers, ethylene-vinyl alcohol copolymers, cellulose diacetate, and ethyl cellulose. Polyester and polyolefine are preferred, and polyester is particularly preferred. More preferred are polyethylene terephthalate and polybutylene terephthalate, and particularly preferred is polybutylene terephthalate.

The nonwoven fabrics can be prepared by either a wet method or a dry method. In terms of obtaining very fine fibers, melt blowing, flash spinning, and forming methods are particularly preferred.

As an example of the method for preparing a nonwoven fabric, an exemplary melt blowing method is described below. After melting in an extruder, a flowing molten polymer is filtered through an appropriate filter. Then the flow is guided to a molten polymer feed chamber of a melt-blowing die, and subsequently discharged through an orifice nozzle. Concurrently, hot gas fed into a hot gas feed chamber is guided to a hot gas ejection slit formed by the melt-blowing die body and a lip, and is then ejected through the slit to attenuate the discharged molten polymer into very fine fibers. Then such layers of fibers are stacked, whereby a nonwoven fabric is formed. In the preparation, a nonwoven fabric with a desired fiber diameter and mass per unit area (basis weight) can be obtained by appropriately selecting and controlling spinning factors such as the resin viscosity, the melt temperature, the discharge amount per hole, the hot gas temperature, the hot gas pressure, and the distance between the spinnerets and the collecting net. In this manner, the fiber orientation and fiber dispersibility can also be controlled. Furthermore, if heat pressing is performed, the thickness and the average pore size of the nonwoven fabric can be controlled.

The leukocyte depletion filter material features an average fiber diameter of 0.30 to 1.60 μm. The lower limit of the average fiber diameter is preferably 0.40 and more preferably 0.50 μm. With the filter material having an average fiber diameter of smaller than 0.30 μm, it is difficult to stably prepare a nonwoven fabric, and the viscous resistance of blood tends to be very high. Conversely, the upper limit of the average fiber diameter is preferably 1.50 μm, and more preferably 1.40 μm. The filter material with an average fiber diameter of greater than 1.60 μm is likely to have lower leukocyte removal performance.

Here, the viscous resistance of blood can be evaluated based on, for example, the pressure loss of a filter. The leukocyte removal performance can be evaluated based on, for example, the leukocyte removal rate.

The average fiber diameter refers to a value determined by the following procedure. The procedure includes measuring the diameters of randomly selected 100 or more fibers in a scanning electron micrograph of a sample taken from a filter material, and determining the number-average diameter of the fibers.

The leukocyte depletion filter material features a coefficient of variation of fiber diameter of at least 0.40 but not more than 1.20. The lower limit of the coefficient of variation of fiber diameter is preferably 0.45, more preferably 0.50, and still more preferably 0.60. The filter material with a coefficient of variation of less than 0.40 tends to have lower blood permeability. Conversely, the upper limit of the coefficient of variation of fiber diameter is preferably 1.00, and more preferably 0.80. The filter material with a coefficient of variation of fiber diameter of more than 1.20 tends to have low leukocyte removal performance. Here, the blood permeability can be evaluated based on, for example, the filtration time.

The coefficient of variation of fiber diameter refers to a value determined by the following procedure. The procedure includes measuring the diameters of randomly selected 100 or more fibers in a scanning electron micrograph of a sample taken from a filter material, and dividing the standard deviation of the diameters by the average fiber diameter.

The lower limit of the average pore size of the leukocyte depletion filter material is preferably 4.0 μm, more preferably 5.0 μm, and still more preferably about 6.0 μm. The filter material with an average pore size of smaller than 4.0 μm tends to have lower blood permeability. Conversely, the upper limit of the average pore size is preferably 20.0 μm, more preferably 15.0 μm, still more preferably 10.0 μm, and most preferably 8.0 μm. The filter material with an average pore size of greater than 20.0 μm tends to have lower leukocyte removal performance.

The average pore size of a filter material refers to a mean flow pore size measured using a perm porometer (product of PMI).

The lower limit of the bulk density of the leukocyte depletion filter material is preferably 0.05 $g/cm^3$, more preferably 0.10 $g/cm^3$, and still more preferably 0.15 $g/cm^3$. The filter material with a bulk density of lower than 0.05 $g/cm^3$ is likely to allow leukocytes to pass through it, so that the leukocyte removal performance tends to be reduced. Conversely, the upper limit of the bulk density is preferably 0.40 $g/cm^3$, more preferably 0.35 $g/cm^3$, and still more preferably 0.30 $g/cm^3$. The filter material with a bulk density of higher than 0.40 $g/cm^3$ tends to have tight fiber spacing so that not only leukocytes but also red blood cells are likely to be captured within the filter. Here, the bulk density refers to a value obtained by measuring the weight per cubic centimeter of a filter material.

The surface of the filter material is preferably modified by a treatment such as graft polymerization, polymer coating, chemical treatment with an alkali, acid or the like, and plasma treatment. Particularly, polymer coating is preferred because it is a simple, excellent method for modifying the surface of a polymer material so as to form a preferred structure.

The polymer to be used for the surface coating may be any hydrophilic polymer that does not have an especially large effect on blood components. For example, copolymers of a monomer containing a hydrophilic functional group (e.g., hydroxyethyl (meth)acrylate) and dimethylaminoethyl (meth)acrylate or diethylaminoethyl (meth)acrylate which contains a basic functional group, and polyvinyl pyrrolidone are particularly preferred because they give hydrophilicity to the material surface to improve the wettability of a filtering medium, and they also introduce charged functional groups to improve blood cell capturing performance.

The method for coating the filter supporting substrate with the polymer may be any of various methods that are capable of uniformly coating the surface of the filter supporting substrate within a certain range without badly clogging the pores of the filter supporting substrate. Examples of such methods include a method of impregnating a filter supporting substrate with a solution of a polymer, a method of spraying a filter supporting substrate with a solution of a polymer, and a method of applying/transferring a solution of a polymer to a filter supporting substrate using a gravure roll coater or the like. Among these, the method of impregnating a filter supporting substrate with a solution of a polymer is preferred for its excellent continuous productivity and low cost.

The solvent for dissolving the polymer may be any solvent that does not significantly dissolve the filter supporting substrate. Examples of such a solvent include amides such as N,N-dimethylformamide and N,N-dimethylacetamide; sulfoxides such as dimethyl sulfoxide; alcohols such as methanol, ethanol, propanol, and butanol; ketones such as acetone and methyl ethyl ketone; esters such as methyl acetate and ethyl acetate; hydrocarbons such as toluene and cyclohexane; halogenated hydrocarbons such as chloroform and dichloromethane; water; and mixtures of these solvents provided that they can dissolve the polymer. Preferred are alcohols such as methanol, ethanol, propanol, and butanol, and particularly preferred are methanol and ethanol.

The leukocyte-containing fluid refers to whole blood, bone marrow, cord blood, menstrual blood, or a tissue extract, and may be fluid roughly separated from any of these. Also, the animal species as the source of the leukocyte-containing fluid is not particularly limited and may be any mammal, including humans, bovines, mice, rats, pigs, apes, dogs, and cats.

The leukocyte depletion filter of the present invention refers to a device that includes the leukocyte depletion filter material of the present invention that is at least packed in a receptacle with fluid inlet and outlet appropriately.

The receptacle may be in any form, including spheres, containers, cassettes, bags, tubes, and columns. For example, preferred are forms such as transparent or translucent cylindrical receptacles with a volume of about 0.1 to 1000 mL and a diameter of about 0.1 to 15 cm, and quadrangular prism-shaped receptacles having a square or rectangular face with about 0.1 to 20 cm sides and a thickness of about 0.1 to 5 cm.

The filter material may be packed in the receptacle, in the form of a single layer or a laminate of layers oriented in the flow direction of the leukocyte-containing fluid. The lower limit of the number of laminated layers of the filter material is 1, and is preferably 5, and more preferably 10, in terms of the leukocyte removal performance. Conversely, the upper limit of the number of laminated layers of the filter material is preferably 100, more preferably 70, and still more preferably 50. If the number of laminated layers of the filter material is more than 100, the blood permeability tends to decrease.

The leukocyte depletion filter may further include a different leukocyte depletion filter material located upstream and/or downstream of the leukocyte depletion filter material. Examples of the different leukocyte depletion filter material include leukocyte depletion filter materials including fibers that have a greater average fiber diameter than the main filter material. If a leukocyte depletion filter material including fibers with a greater average fiber diameter than the main filter material is located on the upstream side, effects such as further improvement of blood permeability are expected. When two different leukocyte depletion filter materials with different average fiber diameters of fibers are used, the filter material located on the downstream side is referred to as a first leukocyte depletion filter material, and the filter material located on the upstream side is referred to as a second leukocyte depletion filter material.

In the case of using two different leukocyte depletion filter materials, the effect of further improving the blood permeability can be achieved when the second leukocyte depletion filter material is located upstream of the first leukocyte depletion filter material, and the second leukocyte depletion filter material includes fibers that have an average fiber diameter of 1.00 to 4.00 μm, where the average fiber diameter is greater than that of the first leukocyte depletion filter material.

The lower limit of the average fiber diameter of the fibers included in the second leukocyte depletion filter material is preferably 1.00 μm, more preferably 1.20 μm, and still more preferably 1.50 μm. The filter material with an average fiber diameter of smaller than 1.00 μm, tends to show a low rate of improvement in blood permeability. Conversely, the upper limit of the average fiber diameter is preferably 4.00 μm, more preferably 3.00 μm, and still more preferably 2.50 μm. The filter material with an average fiber diameter of greater than 4.00 μm tends to show a low rate of improvement in blood permeability.

If the following formulas (a) and/or (b) are satisfied, the fluid permeability in treating blood stored at room temperature or at temperatures close to body temperature can be improved, and the fluid permeability in treating refrigerated blood can also be improved:

$$A \geq 0.40, \text{ and } |A-B| < 0.30 \quad (a)$$

$$B \geq 0.30, \text{ and } 0.10 \leq A \times B \leq 1.00 \quad (b)$$

wherein A represents a coefficient of variation of fiber diameter of the first filter material, and B represents a coefficient of variation of fiber diameter of the second filter material.

The absolute value of the difference between the coefficient of variation of the first filter and the coefficient of variation of the second filter is preferably less than 0.30, more preferably less than 0.26, still more preferably less than 0.24, and most preferably less than 0.22. If the absolute value of the difference between the coefficient of variation of the first filter and the coefficient of variation of the second filter is 0.30 or more, the rate of improvement in blood permeability tends to be reduced.

The product of the coefficient of variation of the first filter and the coefficient of variation of the second filter is preferably at least 0.10 but not more than 1.00, more preferably at least 0.12 but not more than 0.50, still more preferably at least 0.14 but not more than 0.40, and most preferably at least 0.14 but not more than 0.33. If the product of the coefficient of variation of the first filter and the coefficient of variation of the second filter is less than 0.10 or is more than 1.00, the rate of improvement in blood permeability tends to be reduced.

Also, many leukocyte-containing fluids contain fine aggregates, and thus the aggregates are preferably removed by a prefilter. The prefilter is, for example, preferably a fiber assembly with an average fiber diameter of 3 to 50 μm, or a continuous porous material having pores with an average pore size of 20 to 200 μm.

The leukocyte depletion system of the present invention features the leukocyte depletion filter, a blood collection bag connected upstream of the leukocyte depletion filter, and at least one blood bag connected downstream of the leukocyte depletion filter. The blood collection bag refers to, for example, a bag which is connected to a blood collecting tube provided with a blood collecting needle and in which an anticoagulant is enclosed. It may be any blood collection bag generally used for blood collection. The blood bag refers to a bag for storing blood such as whole blood, red cell concentrates, platelet concentrates, and plasma, and may be any commonly used blood bag.

The leukocyte depletion method according to the present invention features a step of removing leukocytes using the leukocyte depletion filter mentioned above.

The leukocyte depletion method preferably includes a step of adding an anticoagulant to a leukocyte-containing fluid to prevent coagulation of the leukocyte-containing fluid, before the step of removing leukocytes using the leukocyte depletion filter. The type of anticoagulant is not particularly limited, and may be, for example, a citrate anticoagulant such as an ACD (acid-citrate-dextrose) solution, a CPD (citrate-phosphate-dextrose) solution, or a CPDA (citrate-phosphate-dextrose-adenine) solution. The anticoagulant may also be heparin, low molecular weight heparin, Futhan (nafamostat mesilate), or EDTA.

Specific examples of leukocytes to be removed by the leukocyte depletion method include neutrophilic leukocytes, acidophilic leukocytes, basophilic leukocytes, lymphocytes, and monocytes.

Hereinafter, the present invention is described in greater detail, referring to examples which, however, are not intended to limit the scope of the present invention.

Example 1

<Nonwoven Fabrics>

The following polyester terephthalate nonwoven fabrics prepared by melt blowing were used.

Prefilter material: Polyethylene terephthalate (hereinafter abbreviated to PET) nonwoven fabric with an average fiber diameter of 15 μm and a mass per unit area of 30 $g/m^2$ Second filter material: Polybutylene terephthalate (hereinafter abbreviated to PBT) nonwoven fabric with an average fiber diameter of 1.51 μm, standard deviation of fiber diameter of 0.75, a coefficient of variation of fiber diameter of 0.50, a mass per unit area of 54 $g/m^2$, an average pore size of 5.8 μm, and a bulk density of 0.18 $g/cm^3$ First filter material: PBT nonwoven fabric with an average fiber diameter of 0.77 μm, a standard deviation of fiber diameter of 0.49, a coefficient of variation of fiber diameter of 0.64, a mass per unit area of 40 $g/m^2$, an average pore size of 5.6 μm, and a bulk density of 0.17 $g/cm^3$ <Preparation of Coating Solution>

To special grade ethanol, 2-hydroxyethyl methacrylate and N,N-diethylaminoethyl methacrylate were added to concentrations of 0.95 mol/L and 0.05 mol/L, respectively. The total amount of the mixture was 300 mL. Then 2,2'-azobis(2,4-dimethylvaleronitrile) (V-65) was added as a polymerization initiator to a concentration of 0.005 mol/L and the mixture was polymerized at 45° C. for 15 hours under nitrogen atmosphere. Then the resulting mixture was poured into an excess of n-hexane to precipitate a polymer, which was then collected. The obtained polymer was dissolved again in ethanol, and the solution was poured into n-hexane so that the polymer was precipitated. The precipitated polymer was dried at 75° C. for four hours, whereby a copolymer of 2-hydroxyethyl methacrylate and N,N-diethylaminoethyl methacrylate (hereinafter abbreviated to HEDE) was obtained. HEDE was dissolved in ethanol to a concentration of 1.0 g/L to prepare an HEDE coating solution.

<Nonwoven Fabric Coating>

The second filter material and the first filter material were immersed in the HEDE coating solution at 20° C. for five minutes, and were then dried in a basket made of stainless steel at 50° C. for 1.5 hours. Next, the nonwoven fabrics were rinsed with water and then dried in a basket made of stainless steel at 50° C. for three hours.

<Preparation of Nonwoven Fabric Disc>

Using a punch, the nonwoven fabrics each were punched into a circle with a diameter of 18 mm, whereby disc-shaped prefilter material, second filter material, and first filter material were prepared.

<Preparation of Filter>

In a cylindrical housing with an inner diameter of 18 mm, 6 layers of prefilter material, 0 layers of second filter material, and 18 layers of first filter material were inserted in the stated order from the inlet side towards the outlet side, whereby a filter was prepared.

The inlet of the filter was connected to a blood storage vessel by a 60-cm-long vinyl chloride tube (outer diameter: 5 mm, inner diameter: 3 mm). The tube was closed with a clamp.

<Filter Evaluation>

To 100 mL of bovine blood was added 14 mL of an ACD-A solution as an anticoagulant (product of Terumo Corporation, formulation: 22 g/L sodium citrate, 8 g/L citric acid, 22 g/L glucose) to prepare a blood sample. The blood sample was warmed to 26° C. in a constant temperature bath. Then 24 mL of the blood sample was put in a blood storage vessel, and subjected to gravity filtration at a drop height of 60 cm, and then 22 mL of the filtered blood was collected in the receiver. The time from the start of filtration until the blood storage vessel was empty was taken as filtration time. The leukocyte concentration before the filtration, and the red blood cell concentration and platelet concentration before and after the filtration were measured using a blood cell counter (product of Sysmex Corp., K-4500). The leukocyte concentration after the filtration was measured using a LeucoCOUNT kit and a FACSCalibur (both are products of Becton, Dickinson and Company) by flow cytometry.

The leukocyte removal rate (−Log), red blood cell recovery rate (%), and platelet removal rate (%) were determined from the following respective formulas:

$$\text{Leukocyte removal rate} = -\text{Log}(b/a)$$

$$\text{Red blood cell recovery rate} = d/c \times 100(\%)$$

$$\text{Platelet removal rate} = (e-f)/e \times 100(\%)$$

wherein a=leukocyte concentration in blood before filtration, b=leukocyte concentration in blood after filtration, c=red blood cell concentration in blood before filtration, d=red blood cell concentration in blood after filtration, e=platelet concentration in blood before filtration, and f=platelet concentration in blood after filtration. The results are shown in Table 1.

Example 2

A filter was prepared in the same manner as in Example 1, except that the first filter material was a PBT nonwoven fabric with an average fiber diameter of 0.77 μm, a standard deviation of fiber diameter of 0.49, a coefficient of variation of fiber diameter of 0.64, a mass per unit area of 40 g/m$^2$, an average pore size of 6.0 μm, and a bulk density of 0.17 g/cm$^3$, and 18 layers of first filter material were used. The prepared filter was evaluated in the same manner as in Example 1. The results are shown in Table 1.

Example 3

A filter was prepared in the same manner as in Example 1, except that the first filter material was a PBT nonwoven fabric with an average fiber diameter of 0.89 μm, a standard deviation of fiber diameter of 0.47, a coefficient of variation of fiber diameter of 0.52, a mass per unit area of 40 g/m$^2$, an average pore size of 5.5 μm, and a bulk density of 0.22 g/cm$^3$, and 18 layers of first filter material were used. The prepared filter was evaluated in the same manner as in Example 1. The results are shown in Table 1.

Example 4

A filter was prepared in the same manner as in Example 1, except that the first filter material was a PBT nonwoven fabric with an average fiber diameter of 0.77 μm, a standard deviation of fiber diameter of 0.49, a coefficient of variation of fiber diameter of 0.64, a mass per unit area of 50 g/m$^2$, an average pore size of 5.3 μm, and a bulk density of 0.17 g/cm$^3$, and 15 layers of first filter material were used. The prepared filter was evaluated in the same manner as in Example 1. The results are shown in Table 1.

Example 5

A filter was prepared in the same manner as in Example 1, except that the first filter material was a PBT nonwoven fabric with an average fiber diameter of 0.77 μm, a standard deviation of fiber diameter of 0.49, a coefficient of variation of fiber diameter of 0.64, a mass per unit area of 50 g/m$^2$, an average pore size of 5.7 μm, and a bulk density of 0.16 g/cm$^3$, and 15 layers of first filter material were used. The prepared filter was evaluated in the same manner as in Example 1. The results are shown in Table 1.

Example 6

A filter was prepared in the same manner as in Example 1, except that the first filter material was a PBT nonwoven fabric with an average fiber diameter of 0.77 μm, a standard deviation of fiber diameter of 0.49, a coefficient of variation of fiber diameter of 0.64, a mass per unit area of 50 g/m$^2$, an average pore size of 5.9 μm, and a bulk density of 0.14 g/cm$^3$, and 15 layers of first filter material were used. The prepared filter was evaluated in the same manner as in Example 1. The results are shown in Table 2.

Example 7

A filter was prepared in the same manner as in Example 1, except that the first filter material was a PBT nonwoven fabric with an average fiber diameter of 0.89 μm, a standard deviation of fiber diameter of 0.47, a coefficient of variation of fiber diameter of 0.52, a mass per unit area of 50 g/m$^2$, an average pore size of 6.0 μm, and a bulk density of 0.18 g/cm$^3$, and 15 layers of first filter material were used. The prepared filter was evaluated in the same manner as in Example 1. The results are shown in Table 2.

Example 8

A filter was prepared in the same manner as in Example 1, except that the first filter material was a PBT nonwoven fabric with an average fiber diameter of 0.89 μm, a standard deviation of fiber diameter of 0.58, a coefficient of variation of fiber diameter of 0.66, a mass per unit area of 50 g/m$^2$, an average pore size of 5.5 μm, and a bulk density of 0.19 g/cm$^3$, and 15 layers of first filter material were used. The prepared filter was evaluated in the same manner as in Example 1. The results are shown in Table 2.

Example 9

A filter was prepared in the same manner as in Example 1, except that the first filter material was a PBT nonwoven fabric with an average fiber diameter of 1.04 μm, a standard deviation of fiber diameter of 0.68, a coefficient of variation of fiber diameter of 0.66, a mass per unit area of 40 g/m$^2$, an average pore size of 5.5 μm, and a bulk density of 0.22 g/cm$^3$, and 18 layers of first filter material were used. The prepared filter was evaluated in the same manner as in Example 1. The results are shown in Table 2.

Comparative Example 1

A filter was prepared in the same manner as in Example 1, except that the first filter material was a PET nonwoven fabric with an average fiber diameter of 1.05 μm, a standard deviation of fiber diameter of 0.30, a coefficient of variation of fiber diameter of 0.29, a mass per unit area of 40 g/m$^2$, an average pore size of 5.2 μm, and a bulk density of 0.18 g/cm$^3$, which is used for the commercially available leukocyte depletion filter (Sepacell RZ-2000) from Asahi Kasei Medical Co., Ltd., and 18 layers of first filter material were used. The prepared filter was evaluated in the same manner as in Example 1. The results are shown in Table 2.

Example 10

A filter was prepared in the same manner as in Example 1, except that the first filer material was a PBT nonwoven fabric with an average fiber diameter of 0.99 μm, a standard deviation of fiber diameter of 0.60, a coefficient of variation of fiber diameter of 0.60, a mass per unit area of 51 g/m$^2$, an average pore size of 6.9 μm, and a bulk density of 0.17 g/cm$^3$, and 15 layers of first filter material were used. The prepared filter was evaluated in the same manner as in Example 1. The results are shown in Table 3.

Example 11

A filter was prepared in the same manner as in Example 1, except that the first filter material was a PBT nonwoven fabric with an average fiber diameter of 1.18 μm, a standard deviation of fiber diameter of 0.55, a coefficient of variation of fiber diameter of 0.47, a mass per unit area of 54 g/m$^2$, an average pore size of 6.2 μm, and a bulk density of 0.18 g/cm$^3$, and 15 layers of first filter material were used. The prepared filter was evaluated in the same manner as in Example 1. The results are shown in Table 3.

Example 12

A filter was prepared in the same manner as in Example 1, except that the first filter material was a PBT nonwoven fabric with an average fiber diameter of 1.31 μm, a standard deviation of fiber diameter of 0.66, a coefficient of variation of fiber diameter of 0.51, a mass per unit area of 54 g/m$^2$, an average pore size of 6.5 μm, and a bulk density of 0.18 g/cm$^3$, and 15 layers of first filter material were used. The prepared filter was evaluated in the same manner as in Example 1. The results are shown in Table 3.

Example 13

A filter was prepared in the same manner as in Example 1, except that the first filter material was a PBT nonwoven fabric with an average fiber diameter of 1.51 μm, a standard deviation of fiber diameter of 0.75, a coefficient of variation of fiber diameter of 0.50, a mass per unit area of 54 g/m$^2$, an average pore size of 5.8 μm, and a bulk density of 0.18 g/cm$^3$, and 15 layers of first filter material were used. The prepared filter was evaluated in the same manner as in Example 1. The results are shown in Table 3.

Comparative Example 2

A filter was prepared in the same manner as in Example 1, except that the first filter material was a PBT nonwoven fabric with an average fiber diameter of 1.65 μm, a standard deviation of fiber diameter of 0.58, a coefficient of variation of fiber diameter of 0.35, a mass per unit area of 53 g/m$^2$, an average pore size of 7.4 μm, and a bulk density of 0.24 g/cm$^3$, and 15 layers of first filter material were used. The prepared filter was evaluated in the same manner as in Example 1. The results are shown in Table 3.

Example 14

A filter was prepared in the same manner as in Example 1, except that the second filter material was a PBT nonwoven fabric with an average fiber diameter of 1.51 μm, a standard deviation of fiber diameter of 0.75, a coefficient of variation of fiber diameter of 0.50, a mass per unit area of 54 g/m$^2$, an average pore size of 5.8 μm, and a bulk density of 0.18 g/cm$^3$, and 2 layers of second filter material were used, and the first filter material was a PBT nonwoven fabric with an average fiber diameter of 1.31 μm, a standard deviation of fiber diameter of 0.66, a coefficient of variation of fiber diameter of 0.51, a mass per unit area of 54 g/m$^2$, an average pore size of 6.5 μm, and a bulk density of 0.18 g/cm$^3$, and 13 layers of first filter material were used. The prepared filter was evaluated in the same manner as in Example 1. The results are shown in Table 4.

Example 15

A filter was prepared in the same manner as in Example 1, except that the second filter material was a PET nonwoven fabric with an average fiber diameter of 1.53 μm, a standard deviation of fiber diameter of 0.47, a coefficient of variation of fiber diameter of 0.30, a mass per unit area of 70 g/m$^2$, an average pore size of 7.0 μm, and a bulk density of 0.21 g/cm$^3$, and 2 layers of second filter material were used, and the first filter material was a PBT nonwoven fabric with an average fiber diameter of 1.31 μm, a standard deviation of fiber diameter of 0.66, a coefficient of variation of fiber diameter of 0.51, a mass per unit area of 54 g/m$^2$, an average pore size of 6.5 μm, and a bulk density of 0.18 g/cm$^3$, and 13 layers of first filter material were used. The prepared filter was evaluated in the same manner as in Example 1. The results are shown in Table 4.

Comparative Example 3

A filter was prepared in the same manner as in Example 1, except that the second filter material was a PET nonwoven fabric with an average fiber diameter of 1.53 μm, a standard deviation of fiber diameter of 0.47, a coefficient of variation of fiber diameter of 0.30, a mass per unit area of 70 g/m$^2$, an average pore size of 7.0 μm, and a bulk density of 0.21 g/cm$^3$, and 2 layers of second filter material were used, and the first filter material was a PET nonwoven fabric with an average fiber diameter of 1.05 μm, a standard deviation of fiber diameter of 0.30, a coefficient of variation of fiber diameter of 0.29, a mass per unit area of 40 g/m$^2$, an average pore size of 5.2 μm, and a bulk density of 0.18 g/cm$^3$, and 16 layers of first filter material were used. The prepared filter was evaluated in the same manner as in Example 1. The results are shown in Table 4.

Example 16

A filter was prepared in the same manner as in Example 1, except that the second filter material was a PET nonwoven fabric with an average fiber diameter of 1.80 μm, a standard deviation of fiber diameter of 1.15, a coefficient of variation of fiber diameter of 0.64, a mass per unit area of 70 g/m$^2$, an average pore size of 7.7 μm, and a bulk density of 0.20 g/cm$^3$, and 2 layers of second filter material were used, and the first filter material was a PBT nonwoven fabric with an average fiber diameter of 1.31 μm, a standard deviation of fiber diameter of 0.66, a coefficient of variation of fiber diameter of 0.51, a mass per unit area of 54 g/m$^2$, an average pore size of 6.5 μm, and a bulk density of 0.18 g/cm$^3$, and 13 layers of first filter material were used. The prepared filter was evaluated in the same manner as in Example 1. The results are shown in Table 4.

Example 17

A filter was prepared in the same manner as in Example 1, except that the second filter material was a PET nonwoven fabric with an average fiber diameter of 1.80 μm, a standard deviation of fiber diameter of 1.15, a coefficient of variation of fiber diameter of 0.64, a mass per unit area of 70 g/m$^2$, an average pore size of 7.7 μm, and a bulk density of 0.20 g/cm$^3$, and 2 layers of second filter material were used, and the first filter material was a PBT nonwoven fabric with an average fiber diameter of 1.18 μm, a standard deviation of fiber diameter of 0.55, a coefficient of variation of fiber diameter of 0.47, a mass per unit area of 54 g/m$^2$, an average pore size of 5.2 μm, and a bulk density of 0.22 g/cm$^3$, and 13 layers of first filter material were used. The prepared filter was evaluated in the same manner as in Example 1. The results are shown in Table 4.

Example 18

A filter was prepared in the same manner as in Example 1, except that the second filter material was a PET nonwoven fabric with an average fiber diameter of 2.46 μm, a standard deviation of fiber diameter of 1.13, a coefficient of variation of fiber diameter of 0.46, a mass per unit area of 70 g/m$^2$, an average pore size of 10.1 μm, and a bulk density of 0.20 g/cm$^3$, and 2 layers of second filter material were used, and the first filter material was a PBT nonwoven fabric with an average fiber diameter of 1.31 μm, a standard deviation of fiber diameter of 0.66, a coefficient of variation of fiber diameter of 0.51, a mass per unit area of 54 g/m$^2$, an average pore size of 6.5 μm, and a bulk density of 0.18 g/cm$^3$, and 13 layers of first filter material were used. The prepared filter was evaluated in the same manner as in Example 1. The results are shown in Table 5.

Comparative Example 4

A filter was prepared in the same manner as in Example 1, except that the second filter material was a PET nonwoven fabric with an average fiber diameter of 10.80 μm, a standard deviation of fiber diameter of 0.45, a coefficient of variation of fiber diameter of 0.04, a mass per unit area of 30 g/m$^2$, an average pore size of 54.7 μm, and a bulk density of 0.19 g/cm$^3$, and 4 layers of second filter material were used, and the first filter material was a PBT nonwoven fabric with an average fiber diameter of 1.31 μm standard deviation of fiber diameter of 0.66, a coefficient of variation of fiber diameter of 0.51, a mass per unit area of 54 g/m$^2$, an average pore size of 6.5 μm, and a bulk density of 0.18 g/cm$^3$, and 13 layers of first filter material were used. The prepared filter was evaluated in the same manner as in Example 1. The results are shown in Table 5.

TABLE 1

| | | | | Example 1 | Example 2 | Example 3 | Example 4 | Example 5 |
|---|---|---|---|---|---|---|---|---|
| Second filter material | Fiber diameter | Average value | AV (μm) | | | | | |
| | | Standard deviation | STD | | | | | |
| | | Coefficient of variation | STD/AV | | | | | |
| | | Mass per unit area | g/m$^2$ | | | | | |
| | | Average pore size | μm | | | | | |
| | | Bulk density | g/cm$^3$ | | | | | |
| First filter material | Fiber diameter | Average value | AV (μm) | 0.77 | 0.77 | 0.89 | 0.77 | 0.77 |
| | | Standard deviation | STD | 0.49 | 0.49 | 0.47 | 0.49 | 0.49 |
| | | Coefficient of variation | STD/AV | 0.64 | 0.64 | 0.52 | 0.64 | 0.64 |
| | | Mass per unit area | g/m$^2$ | 40 | 40 | 40 | 50 | 50 |
| | | Average pore size | μm | 5.6 | 6.0 | 5.5 | 5.3 | 5.7 |
| | | Bulk density | g/cm$^3$ | 0.17 | 0.17 | 0.22 | 0.17 | 0.16 |
| | | Blood | Kind | Bovine | Bovine | Bovine | Bovine | Bovine |
| | | Blood temperature | ° C. | 26 | 26 | 26 | 26 | 26 |
| | | Leukocyte removal rate | −Log | 5.18 | 4.86 | 5.18 | 4.28 | >5.48 |
| | | Red blood cell recovery rate | % | 100 | 100 | 98 | 98 | 98 |

TABLE 1-continued

| | | Example 1 | Example 2 | Example 3 | Example 4 | Example 5 |
|---|---|---|---|---|---|---|
| Platelet removal rate | % | 100 | 100 | 100 | 100 | 100 |
| Filtration time | min | 39.0 | 39.3 | 41.0 | 41.0 | 30.0 |

TABLE 2

| | | | | Example 6 | Example 7 | Example 8 | Example 9 | Comparative Example 1 |
|---|---|---|---|---|---|---|---|---|
| Second filter material | Fiber diameter | Average value | AV (μm) | | | | | |
| | | Standard deviation | STD | | | | | |
| | | Coefficient of variation | STD/AV | | | | | |
| | | Mass per unit area | $g/m^2$ | | | | | |
| | | Average pore size | μm | | | | | |
| | | Bulk density | $g/cm^3$ | | | | | |
| First filter material | Fiber diameter | Average value | AV (μm) | 0.77 | 0.89 | 0.89 | 1.04 | 1.05 |
| | | Standard deviation | STD | 0.49 | 0.47 | 0.58 | 0.68 | 0.30 |
| | | Coefficient of variation | STD/AV | 0.64 | 0.52 | 0.66 | 0.66 | 0.29 |
| | | Mass per unit area | $g/m^2$ | 50 | 50 | 50 | 40 | 40 |
| | | Average pore size | μm | 5.9 | 6.0 | 5.5 | 5.5 | 5.2 |
| | | Bulk density | $g/cm^3$ | 0.14 | 0.18 | 0.19 | 0.22 | 0.18 |
| | | Blood | Kind | Bovine | Bovine | Bovine | Bovine | Bovine |
| | | Blood temperature | ° C. | 26 | 26 | 26 | 26 | 26 |
| | | Leukocyte removal rate | −Log | 4.67 | 4.57 | 4.86 | 5.18 | 4.77 |
| | | Red blood cell recovery rate | % | 98 | 99 | 100 | 100 | 99 |
| | | Platelet removal rate | % | 100 | 100 | 100 | 100 | 92 |
| | | Filtration time | min | 21.3 | 7.8 | 36.4 | 23.0 | 65.0 |

TABLE 3

| | | | | Example 10 | Example 11 | Example 12 | Example 13 | Comparative Example 2 |
|---|---|---|---|---|---|---|---|---|
| Second filter material | Fiber diameter | Average value | AV (μm) | | | | | |
| | | Standard deviation | STD | | | | | |
| | | Coefficient of variation | STD/AV | | | | | |
| | | Mass per unit area | $g/m^2$ | | | | | |
| | | Average pore size | μm | | | | | |
| | | Bulk density | $g/cm^3$ | | | | | |
| First filter material | Fiber diameter | Average value | AV (μm) | 0.99 | 1.18 | 1.31 | 1.51 | 1.65 |
| | | Standard deviation | STD | 0.60 | 0.55 | 0.66 | 0.75 | 0.58 |
| | | Coefficient of variation | STD/AV | 0.60 | 0.47 | 0.51 | 0.50 | 0.35 |
| | | Mass per unit area | $g/m^2$ | 51 | 54 | 54 | 54 | 53 |
| | | Average pore size | μm | 6.9 | 6.2 | 6.5 | 5.8 | 7.4 |
| | | Bulk density | $g/cm^3$ | 0.17 | 0.18 | 0.18 | 0.18 | 0.24 |
| | | Blood | Kind | Bovine | Bovine | Bovine | Bovine | Bovine |
| | | Blood temperature | ° C. | 26 | 26 | 26 | 26 | 26 |
| | | Leukocyte removal rate | −Log | 4.77 | 5.18 | 5.18 | >5.48 | 3.67 |
| | | Red blood cell recovery rate | % | 100 | 100 | 100 | 100 | 100 |
| | | Platelet removal rate | % | 100 | 100 | 100 | 100 | 100 |
| | | Filtration time | min | 32.5 | 32.6 | 33.5 | 32.1 | 44.8 |

TABLE 4

| | | | | Example 14 | Example 15 | Comparative Example 3 | Example 16 | Example 17 |
|---|---|---|---|---|---|---|---|---|
| Second filter material | Fiber diameter | Average value | AV (μm) | 1.51 | 1.53 | 1.53 | 1.80 | 1.80 |
| | | Standard deviation | STD | 0.75 | 0.47 | 0.47 | 1.15 | 1.15 |
| | | Coefficient of variation [B] | STD/AV | 0.50 | 0.30 | 0.30 | 0.64 | 0.64 |
| | | Mass per unit area | $g/m^2$ | 54 | 70 | 70 | 70 | 70 |

TABLE 4-continued

| | | | | Example 14 | Example 15 | Comparative Example 3 | Example 16 | Example 17 |
|---|---|---|---|---|---|---|---|---|
| | | Average pore size | μm | 5.8 | 7.0 | 7.0 | 7.7 | 7.7 |
| | | Bulk density | $g/cm^3$ | 0.18 | 0.21 | 0.21 | 0.20 | 0.20 |
| First filter material | Fiber diameter | Average value | AV (μm) | 1.31 | 1.31 | 1.05 | 1.31 | 1.18 |
| | | Standard deviation | STD | 0.66 | 0.66 | 0.30 | 0.66 | 0.55 |
| | | Coefficient of variation [A] | STD/AV | 0.51 | 0.51 | 0.29 | 0.51 | 0.47 |
| | | Mass per unit area | $g/m^2$ | 54 | 54 | 40 | 54 | 54 |
| | | Average pore size | μm | 6.5 | 6.5 | 5.2 | 6.5 | 5.2 |
| | | Bulk density | $g/cm^3$ | 0.18 | 0.18 | 0.18 | 0.18 | 0.22 |
| | | $\lvert A - B \rvert$ | | 0.01 | 0.21 | 0.01 | 0.13 | 0.17 |
| | | A × B | | 0.26 | 0.15 | 0.09 | 0.33 | 0.30 |
| | | Blood | Kind | Bovine | Bovine | Bovine | Bovine | Bovine |
| | | Blood temperature | ° C. | 26 | 26 | 26 | 26 | 26 |
| | | Leukocyte removal rate | −Log | 5.18 | 5.18 | 4.16 | >5.48 | >5.48 |
| | | Red blood cell recovery rate | % | 100 | 100 | 100 | 100 | 100 |
| | | Platelet removal rate | % | 100 | 100 | 88 | 100 | 100 |
| | | Filtration time | min | 10.8 | 10.1 | 17.9 | 7.4 | 8.1 |

TABLE 5

| | | | | Example 18 | Comparative Example 4 |
|---|---|---|---|---|---|
| Second filter material | Fiber diameter | Average value | AV (μm) | 2.46 | 10.80 |
| | | Standard deviation | STD | 1.13 | 0.45 |
| | | Coefficient of variation [B] | STD/AV | 0.46 | 0.04 |
| | | Mass per unit area | $g/m^2$ | 70 | 30 |
| | | Average pore size | μm | 10.1 | 54.7 |
| | | Bulk density | $g/cm^3$ | 0.20 | 0.19 |
| First filter material | Fiber diameter | Average value | AV (μm) | 1.31 | 1.31 |
| | | Standard deviation | STD | 0.66 | 0.66 |
| | | Coefficient of variation [A] | STD/AV | 0.51 | 0.51 |
| | | Mass per unit area | $g/m^2$ | 54 | 54 |
| | | Average pore size | μm | 6.5 | 6.5 |
| | | Bulk density | $g/cm^3$ | 0.18 | 0.18 |
| | | $\lvert A - B \rvert$ | | 0.05 | 0.47 |
| | | A × B | | 0.23 | 0.02 |
| | | Blood | Kind | Bovine | Bovine |
| | | Blood temperature | ° C. | 26 | 26 |
| | | Leukocyte removal rate | −Log | 5.18 | 5.18 |
| | | Red blood cell recovery rate | % | 100 | 100 |
| | | Platelet removal rate | % | 100 | 100 |
| | | fFiltration time | min | 6.9 | 31.5 |

The results in Tables 1 to 5 show that the filter materials with a small average fiber diameter and a high coefficient of variation of fiber diameter have both high leukocyte removal performance and high blood permeability. The results also show that the blood permeability is higher when the first filter material has a small average fiber diameter and a high coefficient of variation of fiber diameter and the second filter material which has a greater average fiber diameter than that of the first filter material is located upstream of the first filter material.

Example 19

<Nonwoven Fabrics>

The following polyester terephthalate nonwoven fabrics prepared by melt blowing were used.

Prefilter material: PET nonwoven fabric with an average fiber diameter of 15 μm and a mass per unit area of 30 $g/m^2$ Second filter material: PBT nonwoven fabric with an average fiber diameter of 1.51 μm, a standard deviation of fiber diameter of 0.75, a coefficient of variation of fiber diameter of 0.50, a mass per unit area of 54 $g/m^2$, an average pore size of 5.8 μm, and a bulk density of 0.18 $g/cm^3$ First filter material: PBT nonwoven fabric with an average fiber diameter of 1.18 μm, a standard deviation of fiber diameter of 0.55, a coefficient of variation of fiber diameter of 0.47, a mass per unit area of 54 $g/m^2$, an average pore size of 6.2 μm, and a bulk density of 0.18 $g/cm^3$ <Preparation of Coating Solution>

To special grade ethanol, 2-hydroxyethyl methacrylate and N,N-dimethylaminoethyl methacrylate were added to concentrations of 0.95 mol/L and 0.05 mol/L, respectively. The total amount of the mixture was 300 mL. Then 2,2'-azobis(2,4-dimethylvaleronitrile) (V-65) was added as a polymerization initiator to a concentration of 0.005 mol/L and the mixture was polymerized at 45° C. for 15 hours under nitrogen atmosphere. Then the resulting mixture was poured into an excess of n-hexane to precipitate a polymer, which was then collected. The obtained polymer was dissolved again in ethanol, and the solution was poured into n-hexane so that the polymer was precipitated. The precipitated polymer was dried at 75° C. for four hours, whereby a copolymer of 2-hydroxyethyl methacrylate and N,N-dimethylaminoethyl methacrylate (hereinafter abbreviated to HEDM) was obtained. HEDM was dissolved in ethanol to a concentration of 1.0 g/L to prepare an HEDM coating solution.

<Nonwoven Fabric Coating>

The second filter material and the first filter material were immersed in the HEDM coating solution at 20° C. for five minutes, and were then dried in a basket made of stainless steel at 50° C. for 1.5 hours. Next, the nonwoven fabrics were rinsed with water and then dried in a basket made of stainless steel at 50° C. for three hours.

<Preparation of Nonwoven Fabric Disc>

Using a punch, the nonwoven fabrics each were punched into a 7.2 cm×7.2 cm square, whereby square disc-shaped prefilter material, second filter material, and first filter material were prepared.

<Preparation of Filter>

In a 7.2 cm×7.2 cm square housing, 6 layers of prefilter material, 2 layers of second filter material, and 25 layers of first filter material were inserted in the stated order from the inlet side towards the outlet side, whereby a filter was prepared. The inlet of the filter was connected to a blood bag by a 60-cm-long vinyl chloride tube (outer diameter: 5 mm, inner diameter: 3 mm). The tube was closed with a clamp.

<Filter Evaluation>

An amount of 400 mL of bovine whole blood was collected in a blood bag containing 56 mL of the anticoagulant ACD-A solution (product of Terumo Corporation, formulation: 2.20 w/v % sodium citrate hydrate, 0.80 w/v % citrate hydrate, 2.20 w/v % glucose) and they are mixed to prepare a blood sample. The blood sample was warmed to 26° C. in a constant temperature bath, and then subjected to gravity filtration through the filter at a drop height of 60 cm. As a result of the measurements, the leukocyte removal rate (−Log) was 5.36 or higher (removal rate of not lower than the limit of detection), the red blood cell recovery rate was 100%, the platelet removal rate was 100%, and the filtration time was 8.3 minutes.

Examples 20 to 26 were carried out using human blood.

Example 20

A filter was prepared in the same manner as in Example 1, except that the HEDM coating solution was used, and the first filter material was a PBT nonwoven fabric with an average fiber diameter of 1.18 μm, a standard deviation of fiber diameter of 0.55, a coefficient of variation of fiber diameter of 0.47, a mass per unit area of 54 $g/m^2$, an average pore size of 6.2 μm, and a bulk density of 0.18 $g/cm^3$, and 27 layers of first filter material were used.

<Filter Evaluation>

An amount of 200 mL of human whole blood was collected in a blood bag containing 28 mL of the anticoagulant CPD solution (blood bag CPD from Terumo Corporation, formulation: 2.63 w/v % sodium citrate hydrate, 0.327 w/v % citrate hydrate, 2.32 w/v % glucose, 0.251 w/v % sodium dihydrogen phosphate) and they were mixed to prepare a blood sample. The blood sample was warmed to 26° C. in a constant temperature bath. Then 24 mL of the blood sample was put in a blood storage vessel, and subjected to gravity filtration at a drop height of 60 cm, and then 22 mL of the filtered blood was collected in the receiver. The results are shown in Table 6.

Example 21

A filter was evaluated in the same manner as in Example 20, except that the prepared blood sample was stored in a 4° C. refrigerator, and then subjected to gravity filtration at 4° C. on the day following the blood collection. The results are shown in Table 6.

Example 22

A filter was prepared in the same manner as in Example 21, except that the second filter material was a PBT nonwoven fabric with an average fiber diameter of 1.51 μm, a standard deviation of fiber diameter of 0.75, a coefficient of variation of fiber diameter of 0.50, a mass per unit area of 54 $g/m^2$, an average pore size of 5.8 μm, and a bulk density of 0.18 $g/cm^3$, and 2 layers of second filter material were used, and the first filter material was a PBT nonwoven fabric with an average fiber diameter of 1.18 μm, a standard deviation of fiber diameter of 0.55, a coefficient of variation of fiber diameter of 0.47, a mass per unit area of 54 $g/m^2$, an average pore size of 6.2 μm, and a bulk density of 0.18 $g/cm^3$, and 25 layers of first filter material were used. The prepared filter was evaluated in the same manner as in Example 21. The results are shown in Table 6.

Example 23

A filter was prepared in the same manner as in Example 21, except that the second filter material was a PET nonwoven fabric with an average fiber diameter of 1.53 μm, a standard deviation of fiber diameter of 0.47, a coefficient of variation of fiber diameter of 0.30, a mass per unit area of 70 $g/m^2$, an average pore size of 7.0 μm, and a bulk density of 0.21 $g/cm^3$, and 2 layers of second filter material were used, and the first filter material was a PBT nonwoven fabric with an average fiber diameter of 1.18 μm, a standard deviation of fiber diameter of 0.55, a coefficient of variation of fiber diameter of 0.47, a mass per unit area of 54 $g/m^2$, an average pore size of 6.2 μm, and a bulk density of 0.18 $g/cm^3$, and 25 layers of first filter material were used. The prepared filter was evaluated in the same manner as in Example 21. The results are shown in Table 6.

Example 24

A filter was prepared in the same manner as in Example 21, except that the second filter material was a PBT nonwoven fabric with an average fiber diameter of 1.51 μm, a standard deviation of fiber diameter of 0.75, a coefficient of variation of fiber diameter of 0.50, a mass per unit area of 54 $g/m^2$, an average pore size of 5.8 μm, and a bulk density of 0.18 $g/cm^3$, and 2 layers of second filter material were used, and the first filter material was a PBT nonwoven fabric with an average fiber diameter of 1.31 μm, a standard deviation of fiber diameter of 0.66, a coefficient of variation of fiber diameter of 0.51, a mass per unit area of 54 $g/m^2$, an average pore size of 6.5 μm, and a bulk density of 0.18 $g/cm^3$, and 25 layers of first filter material were used. The prepared filter was evaluated in the same manner as in Example 21. The results are shown in Table 6.

Example 25

A filter was prepared in the same manner as in Example 21, except that the second filter material was a PBT nonwoven fabric with an average fiber diameter of 1.51 μm, a standard deviation of fiber diameter of 0.75, a coefficient of variation of fiber diameter of 0.50, a mass per unit area of 54 $g/m^2$, an average pore size of 5.8 μm, and a bulk density of 0.18 $g/cm^3$, and 2 layers of second filter material were used, and the first filter material was a PBT nonwoven fabric with an average fiber diameter of 0.99 μm, a standard deviation of fiber diameter of 0.60, a coefficient of variation of fiber diameter of 0.60, a mass per unit area of 51 $g/m^2$, an average pore size of 6.9 μm, and a bulk density of 0.17 $g/cm^3$, and 25 layers of first filter material were used. The prepared filter was evaluated in the same manner as in Example 21. The results are shown in Table 6.

Example 26 filter was prepared in the same manner as in Example 21, except that the second filter material was a PET nonwoven fabric with an average fiber diameter of 2.46 μm, a standard deviation of fiber diameter of 1.13, a coefficient of variation of fiber diameter of 0.46, a mass per unit area of 70 $g/m^2$, an average pore size of 10.1 μm, and a bulk density of 0.20 $g/cm^3$, and 2 layers of second filter material were used, and the first filter material was a PBT nonwoven fabric with an average fiber diameter of 0.77 μm, a standard deviation of fiber diameter of 0.49, a coefficient of variation of fiber diameter of 0.64, a mass per unit area of 50 $g/m^2$, an average pore size of 5.7 μm, and a bulk density of 0.16 $g/cm^3$, and 25 layers of first filter material were used. The prepared filter was evaluated in the same manner as in Example 21. The results are shown in Table 6.

comprising fibers that have an average fiber diameter of 0.50 to 1.60 μm and a coefficient of variation of fiber diameter of 0.40 to 0.80, an average pore size of 4.0 to 8.0 μm, and a bulk density of 0.10 to 0.35 $g/cm^3$; and a second leukocyte depletion filter material located upstream of the first leukocyte depletion filter material, the second leukocyte depletion filter material comprising fibers that have an average fiber diameter of 1.20 to 3.00 μm, wherein the average fiber diameter of the fibers of the second leukocyte depletion filter material is greater than the average fiber diameter of the fibers of the first leukocyte depletion filter material, and the first and second leukocyte depletion filter materials satisfy the following formulas (a) and (b):

$$|A-B|\leq 0.21 \quad (a)$$

$$0.15\leq A\times B\leq 0.33 \quad (b)$$

where A represents the coefficient of variation of fiber diameter of the fibers in the first leukocyte depletion filter material, and B represents a coefficient of variation of fiber diameter of the fibers in the second leukocyte depletion filter material.

2. The leukocyte depletion filter according to claim 1, wherein the first leukocyte depletion filter material contains a hydrophilic polymer at least on a surface of the fibers.

3. The leukocyte depletion filter according to claim 1, wherein the first leukocyte depletion filter material is packed in the form of a single layer or a laminate of layers oriented in a fluid flow direction.

TABLE 6

| | | | | Example 20 | Example 21 | Example 22 | Example 23 | Example 24 | Example 25 | Example 26 |
|---|---|---|---|---|---|---|---|---|---|---|
| Second filter material | Fiber diameter | Average value | AV (μm) | | | 1.51 | 1.53 | 1.51 | 1.51 | 2.46 |
| | | Standard deviation | STD | | | 0.75 | 0.47 | 0.75 | 0.75 | 1.13 |
| | | Coefficient of variation [B] | STD/AV | | | 0.50 | 0.30 | 0.50 | 0.50 | 0.46 |
| | Mass per unit area | | $g/m^2$ | | | 54 | 70 | 54 | 54 | 70 |
| | Average pore size | | μm | | 5.8 | 7.0 | 5.8 | 5.8 | 10.1 | |
| | Bulk density | | $g/cm^3$ | | 0.18 | 0.21 | 0.18 | 0.18 | 0.20 | |
| First filter material | Fiber diameter | Average value | AV (μm) | 1.18 | 1.18 | 1.18 | 1.18 | 1.31 | 0.99 | 0.77 |
| | | Standard deviation | STD | 0.55 | 0.55 | 0.55 | 0.55 | 0.66 | 0.60 | 0.49 |
| | | Coefficient of variation [A] | STD/AV | 0.47 | 0.47 | 0.47 | 0.47 | 0.51 | 0.60 | 0.64 |
| | Mass per unit area | | $g/m^2$ | 54 | 54 | 54 | 54 | 54 | 51 | 50 |
| | Average pore size | | μm | 6.2 | 6.2 | 6.2 | 6.2 | 6.5 | 6.9 | 5.7 |
| | Bulk density | | $g/cm^3$ | 0.18 | 0.18 | 0.18 | 0.18 | 0.18 | 0.17 | 0.16 |
| | \|A − B\| | | | | | 0.03 | 0.17 | 0.01 | 0.10 | 0.18 |
| | A × B | | | | | 0.24 | 0.14 | 0.26 | 0.30 | 0.29 |
| | Blood | | Kind | Human | Human | Human | Human | Human | Human | Human |
| | Blood temperature | | ° C. | 26 | 4 | 4 | 4 | 4 | 4 | 4 |
| | Leukocyte removal rate | | −Log | >5.36 | 5.28 | 4.98 | 4.98 | 4.98 | >5.28 | 4.98 |
| | Red blood cell recovery rate | | % | 100 | 100 | 100 | 100 | 100 | 100 | 100 |
| | Platelet removal rate | | % | 100 | 100 | 100 | 100 | 100 | 100 | 100 |
| | Filtration time | | min | 17.2 | 20.9 | 15.5 | 16.1 | 15.1 | 19.5 | 16.5 |

The results in Table 6 show that the blood permeability for blood stored at 4° C. is not reduced when the first filter material has a small average fiber diameter and a high coefficient of variation of fiber diameter and the second filter material which has a greater average fiber diameter than that of the first filter material is located upstream of the first filter material.

The invention claimed is:

1. A leukocyte depletion filter, comprising:

a receptacle having fluid inlet and outlet;

a first leukocyte depletion filter material packed in the receptacle, the first leukocyte depletion filter material

4. The leukocyte depletion filter according to claim 1, further comprising a prefilter material for removal of fine aggregates, located upstream of the leukocyte depletion filter material.

5. A leukocyte depletion system, comprising:

a leukocyte depletion filter, comprising:

a receptacle having fluid inlet and outlet;

a first leukocyte depletion filter material packed in the receptacle, the first leukocyte depletion filter material comprising fibers that have an average fiber diameter of 0.50 to 1.60 μm and a coefficient of variation of fiber diameter of 0.40 to 0.80, an average pore size of 4.0 to 8.0 μm, and a bulk density of 0.10 to 0.35 g/cm$^3$; and a second leukocyte depletion filter material located upstream of the first leukocyte depletion filter material, the second leukocyte depletion filter material comprising fibers that have an average fiber diameter of 1.20 to 3.00 μm, wherein the average fiber diameter of the fibers of the second leukocyte depletion filter material is greater than the average fiber diameter of the fibers of the first leukocyte depletion filter material, and the first and second leukocyte depletion filter materials satisfy the following formulas (a) and (b):

$$|A-B| \leq 0.21 \quad \text{(a)}$$

$$0.15 \leq A \times B \leq 0.33 \quad \text{(b)}$$

where A represents the coefficient of variation of fiber diameter of the fibers in the first leukocyte depletion filter material, and B represents a coefficient of variation of fiber diameter of the fibers in the second leukocyte depletion filter material;

a blood collection bag connected upstream of the leukocyte depletion filter via the fluid inlet; and at least one blood bag connected downstream of the leukocyte depletion filter via the fluid outlet.

* * * * *